United States Patent [19]

Marchionni et al.

[11] Patent Number: 5,164,517

[45] Date of Patent: Nov. 17, 1992

[54] PROCESS FOR PREPARING FLUOROPOLYETHERS AND PERFLUOROPOLYETHERS HAVING NEUTRAL OR FUNCTIONAL END GROUPS AND A CONTROLLED MOLECULAR WEIGHT

[75] Inventors: Giuseppe Marchionni; Guglielmo Gregorio; Ugo De Patto; Mario Padovan, all of Milan, Italy

[73] Assignee: Ausimont S.p.A., Milan, Italy

[21] Appl. No.: 647,084

[22] Filed: Jan. 29, 1991

[30] Foreign Application Priority Data

Jan. 31, 1990 [IT] Italy .................. 19301 A/90

[51] Int. Cl.⁵ ................ C07D 319/12; C07C 41/01
[52] U.S. Cl. .................. 549/380; 568/392; 568/394; 568/604; 568/615; 562/849; 562/850
[58] Field of Search ........... 568/604, 615, 392, 394; 562/849, 850; 549/380

[56] References Cited

U.S. PATENT DOCUMENTS

| | | |
|---|---|---|
| 3,242,218 | 3/1966 | Miller . |
| 3,250,808 | 5/1966 | Moore et al. . |
| 3,665,041 | 5/1972 | Sianesi et al. . |
| 3,715,378 | 2/1973 | Sianesi et al. . |
| 3,847,978 | 11/1974 | Sianesi et al. . |
| 4,532,039 | 7/1985 | Ito . |

FOREIGN PATENT DOCUMENTS

| | | |
|---|---|---|
| 148482 | 7/1985 | European Pat. Off. . |
| 151877 | 8/1985 | European Pat. Off. . |
| 167258 | 1/1986 | European Pat. Off. . |
| 191490 | 8/1986 | European Pat. Off. . |
| 223238 | 5/1987 | European Pat. Off. . |
| 224201 | 6/1987 | European Pat. Off. . |
| 1104492 | 2/1968 | United Kingdom . |
| 1226566 | 3/1971 | United Kingdom . |
| 87/00538 | 1/1987 | World Int. Prop. O. . |
| 87/02992 | 5/1987 | World Int. Prop. O. . |

*Primary Examiner*—Howard T. Mars
*Attorney, Agent, or Firm*—Morgan & Finnegan

[57] ABSTRACT

This invention relates to a process for preparing fluoropolyethers and perfluoropolyethers having neutral and/or functional end groups and a lower molecular weight by a selective catalytic cleavage of the corresponding higher molecular weight fluoropolyethers and perfluoropolyethers, characterized in that said cleavage is carried out by operating in the presence of a catalyst system consisting of a combination of silicon dioxide with at least an oxide, a fluoride or an oxyfluoride of a metal selected from Al, Ti, V, Cr, Co, Fe, Ni, Mo, Zn, Cu, Cd, Mn, Sb, Sn, Zr, Sc, Y, La and homologs thereof, Pb, Mg, W.

14 Claims, No Drawings

PROCESS FOR PREPARING FLUOROPOLYETHERS AND PERFLUOROPOLYETHERS HAVING NEUTRAL OR FUNCTIONAL END GROUPS AND A CONTROLLED MOLECULAR WEIGHT

FIELD OF THE INVENTION

The present invention relates to the preparation of fluoropolyethers and perfluoropolyethers having neutral and/or functional end groups and exhibiting a lower controlled molecular weight starting from the corresponding higher molecular weight fluoropolyethers and perfluoropolyethers.

In particular, the present invention relates to an improved process for the selective catalytic separation of high molecular weight fluoropolyethers and perfluoropolyethers in order to obtain fluoropolyethers and perfluoropolyethers having neutral or functional end groups and exhibiting a lower and selectively modifiable molecular weight.

More in particular, the present invention relates to the catalytic separation of high molecular weight fluoropolyethers and perfluoropolyethers, obtained for example by photooxidation of perfluoroolefins or by polymerization processes with opening of the ring of partially fluorinated oxethane compounds or by fluorination of oxidized hydrogenated polyalkylene compounds, etc.

It is generally known that the methods employed for preparing the abovesaid fluoropolyethers and perfluoropolyethers lead to the obtainment of final products having, for the most part, a too high molecular weight (see for example British patents 1,226,566 and 1,104,482 and U.S. Pat. No. 3,250,808).

These high molecular weight products have limited practical applications. In fact, among the most interesting applications there are the ones in the electronic sector, wherein very low molecular weights of the perfluoropolyethers are required, and in the field of the operational fluids, for example for high-vacuum pumps, wherein also the use of mean molecular weight perfluoropolyethers is possible.

Thus, processes have been described for the catalytic decomposition or cleavage of high molecular weight perfluoropolyethers in order to obtain perfluoropolyethers having a reduced high molecular weight.

BACKGROUND OF THE INVENTION

European patents EP-167.258 and EP-223.238 describe catalytic cleavage processes, in which certain perfluoropolyethers are catalytically separated by heat, thereby obtaining products having a reduced molecular weight and the same chain structure as the starting products, in the form of mixtures of compounds with both neutral and acid end groups. There are utilized fluorides and oxyfluorides of transition metals such as Ti, V, Cr, Mn, Fe, Co, Ni, Cu, Zr, Mo, Zn, or of Al, Sn, Sb or precursors thereof, such as bromides, chlorides, oxides (which convert into the fluorinated catalytic species under the process conditions) operating at temperatures ranging from 150° C. to 380° C.

the cleavage can occur at the C-O bond of perfluoropolyethers, thereby obtaining more homogeneous and stable products with high yields (EP-167,258); the cleavage can also take place in chemically stabler points of the chain, if more effective catalyst and high temperatures are used (EP-223,238), operating under heavier products distillation and recycle conditions (EP-223,238).

Nevertheless, the residence times in the reactor are generally such that the substrate can undergo undersirable fragmentations prior to its extraction from the reactor, which are due, in particular, to the cleavage of the end groups, which give rise to gaseous products. Furthermore, the total specific productivity, i.e. the product amount per reaction time unit and per catalyst weight unit, and the duration of the catalyst life are not always satisfactory.

Thus, it was desirable to have available high-efficiency catalysts, such as to permit to increase the reaction rate without having to extend the times of contact with the catalyst, thereby avoiding the main cause for the undesired decomposition reactions which lead to the formation of gaseous products.

DETAILED DESCRIPTION OF THE INVENTION

Thus, it is an object of the present invention to provide an improved process for preparing fluoropolyethers and perfluoropolyethers having neutral and/or functional end groups and having a controlled molecular weight, by a catalytic cleavage of fluoropolyethers and perfluoropolyethers having a higher molecular weight. Another object is that of providing perfluoro-2,5- and -2,6-dimethyl-1,4-dioxane (U.K. 1,051,649) having good solvent properties.

Another object is that of providing a catalytic cleavage process of fluoropolyethers and perfluoropolyethers having a high, selectively modifiable molecular weight to obtain lower molecular weight products having a wider range of uses.

A further object is that of providing a catalyst system endowed with a high specific productivity and a prolonged life.

These and still other objects, which will be more clearly apparent to those skilled in the art from the following description, are achieved, according to the present invention, by a process for producing fluoropolyethers and perfluoropolyethers having neutral and/or functional end groups and a lower molecular weight, by a selective catalytic cleavage of the corresponding higher molecular weight fluoropolyethers and perfluoropolyethers. The process is characterized in that said cleavage is conducted by operating in the presence of a catalyst system consisting of a combination of silicon dioxide with at least an oxide, a fluoride or an oxyfluoride of a metal selected from Al, Ti, V, Cr, Co, Fe, Ni, Mo, Zn, Cu, Cd, Mn, Sb, Sn, Zr, Sc, Y, La and homologs thereof, i.e., the lanthanide series elements, Pb, Mg, W.

It has surprisingly been found that, when operating under the conditions described in the process forming the object of the present invention, the catalyst system activity and life appear unexpectedly higher than the ones obtainable when using the known metal fluorinated catalysts.

Defined more particularly, the catalyst system, in the terms defined hereinbefore, consists of high specific surface materials based on silicon dioxide in combination with at least an oxide, a fluoride or an oxyfluoride of a metal selected from the ones listed hereinbefore.

Thus, it is possible to have binary systems consisting of silicon dioxide and of only another metal oxide, fluoride or oxyfluoride, or ternary or polymetal systems, in which the silicon dioxide is combined with more than one oxide, fluoride or oxyfluoride as defined above.

As mentioned before, in the case of La oxides, fluorides and oxyfluorides, also the relevant homologous elements are to be considered as included in the definition.

Whenever used in the present invention, the definition: silicon dioxide combined with oxides of the abovesaid metals, refers in particular to a mixed oxide of silicon and of said metals, either binary or ternary or polyoxide, for example consisting of:

a) silicates of the above-listed metals in the microcrystalline or amorphous form;
b) amorphous, chemically homogeneous mixtures, for example prepared by: 1) co-precipitation in the form of a gel and subsequent calcination, or 2) hydrolysis of mixtures of the corresponding metal alcoholates and subsequent drying, preferably followed by calcination, and c) one or more metal oxides supported on $SiO_2$, preferably silica gel or amorphous silicas. Said supporting can be obtained by conventional techniques.

Very often said products are already available on the market and/or at any rate preparable, as mentioned before, according to known techniques; refer e.g. to: J. of Non-Crystalline Solids 82 (1986), 97–102; J. Cat. 35 (1974), 225–231; J. Cat. 105, (1987), 511–520; Applied Cat. 32, (1987), 315–326; Langmuir 5, (1987), 563–567.

In like manner, whenever used in the present invention, the definition: silicon dioxide combined with the fluorides and oxyfluorides of the abovesaid metals, refers in particular to fluorides and oxyfluorides carried on silicon dioxide.

Substantially conventional techniques are utilizable for carrying the considered fluorides and oxyfluorides on the silicon dioxide.

In particular, in the case of a fluoride or an oxyfluoride of the abovesaid metals carried on $SiO_2$ it is possible to directly impregnate a silica, for example a silica gel, with the aqueous solution of the fluoride or oxyfluoride of the selected metal or metals, or with the aqueous solution of a salt of said metals, which is capable of easily giving rise to fluoride by treatment with HF or salts thereof, drying and calcination are then carried out, for example at a temperature ranging from 200° to 700° C.

As an alternative, if it is desired to prepare catalysts containing fluorides which are not obtainable from aqueous solutions, an anhydrous porous silica, for example consisting of silicalite or of a silica gel calcined at high temperature (for example at about 900°–1000° C.) is impregnated with an organic solution of a compound, for example a chloride or a bromide, susceptible of converting, after drying, into a fluoride or an oxyfluoride:

a) directly in situ under the reaction conditions, or
b) by treatment with a fluorinating agent compatible with silica, such as $F_2$, hypofluorites, $COF_2$, etc., at temperatures ranging from −50° C. to 100° C., approximately.

For example, a catalyst consisting of $AlF_3$ carried on silica gel is prepared by dissolving hydrated alumina in aqueous HF, by impregnating microporous silica with this solution, and then by drying. In like manner it is operated for $ZrF_4$, using an aqueous solution of $(NH_4)_2ZrF_6$ to impregnate the silica.

For a catalyst consisting of a carried yttrium, lanthanum or zirconium oxyfluoride, it is operated as follows: a silica gel is impregnated with an aqueous solution of lanthanum or yttrium nitrates or of zirconyl nitrate, it is dried at 160° C. and then impregnated once again with an ammonium fluoride aqueous solution in amounts from 2 to 3 fluorine ions per metal atom. It is calcined at 600°–700° C., thereby obtaining a product having the metal for the most part in the form of an oxyfluoride.

A tin fluoride on silica is obtainable by impregnating silica gel, previously calcined at 900° C., with $SnBr_4$ either in the liquid form or dissolved in a volatile solvent. After evaporation of the solvent, the material is treated with gaseous $CF_3OF$, which acts as a mild fluorinating agent, shifts the bromine and gives rise to the carried tin fluoride.

Examples of catalyst systems which have proved to be effective are the following: silica-alumina, also of the commercial type, silica-titanium oxide, aluminium silicates with zeolite structure, in the acid form, silica-chromium oxide, chromium oxide on silica gel, silica-$V_2O_5$, $AlF_3$ on silica, LaOF and $ZrOF_2$ on silica.

In the scope of the definitions given before, the silica content, expressed as $SiO_2$ by weight percent, ranges approximately from 10% to 95% and preferably from 50% to 90%, approximately. Furthermore, the specific surface area of the catalytic combination is usually $\geq 10$ $m^2/g$ and preferably higher than 50 $m^2/g$.

The cleavage reaction is conducted at temperatures ranging approximately from 150° to 380° C., according to substantially conventional operative modes in the known cleavage reactions of this kind.

The catalytic combination is finally suitably introduced in a fine particle form, for example in the form of a fine powder of granules having average sizes below 0.1 mm approximately, thereby promoting a homogeneous dispersion of the catalyst system in the reaction mass.

As regards the amounts of catalytic combination to be utilized, they can vary over a wide range, depending on the various concerned parameters, such as temperature, contact time, utilized high molecular weight perfluoropolyether, metal species contained in the mixed oxides and the like.

Nevertheless it is possible to indicatively state that results of interest are obtained with catalyst combination amounts ranging approximately from 0.1% to 25% by weight, based on the present fluoropolyether or perfluoropolyether, and preferably ranging approximately from 0.5% to 10% by weight.

The perfluoropolyethers and fluoropolyethers having perfluoroalkyl end groups and the ones containing functional end groups, hereinafter referred to, for the sake of simplicity, as functionalized perfluoropolyethers and functionalized fluoropolyethers, are well known in the art and are described, along with the method of preparing them, in several articles, patents and patent applications, among which British patents 1,104,482, 1,226,566; U.S. Pat. Nos. 3,242,218, 3,250,808, 3,665,041, 3,715,378, 3,847,978 and 4,532,039; European patent applications 148,482, 151,877, 191,490 and 224,201; international patent applications WO 87/00538 and WO 87/02992; Italian patent 1,189,469 and the article by D. Sianesi "Polieteri perfluorurati: sinthesi e caratterizzazione di una nuova classe di fluidi inerti" ("Perfluorinated Polyethers: synthesis and characterization of a new class of inert fluids"), La Chimica e l'Industria, 50, February 1968, 206–214.

Many of these perfluoropolyethers are marketed, for example under the trademarks Fomblin ®, Krytox ® and Demnum ®.

The process of the present invention is applicaable in particular to neutral and/or functionalized perfluropolyethers and fluoropolyethers having the formulas:

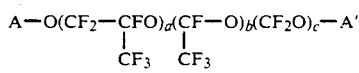

wherein A and A', like or different from each other, represent a perfluoroalkyl group containing from 1 to 3 carbon atoms; $CF_3$, $C_2F_5$, $C_3F_7$; COF, $CF_2COCF_3$, $CF_2COF$ and $CF(CF_3)COF$; and units

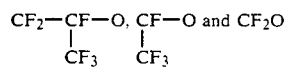

are statistically distributed along the chain; a and c are integers, while b is an integer or zero and the a/b+c ratio varies from 5 to 15; starting from such perfluoropolyethers, there are also obtained fractions of perfluoro-2,5-dimethyl-1,4-dioxane and/or perfluoro-2,6-dimethyl-1,4-dioxane.

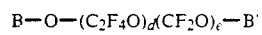

wherein B and B', like or different from each other, represent $CF_3$, $C_2F_5$, COF, $CF_2$-COF, and units $C_2F_4O$ and $CF_2O$ are statistically distributed along the chain; d and e are integers and the d/e ratio varies from 0.3 to 5;

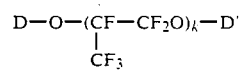

wherein D and D', like or different from each other, represent $C_3F_7$ or

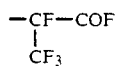

and k is an integer;

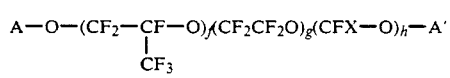

wherein A and A' are the same as defined above, X represents F or $CF_3$; the units

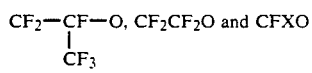

are statistically distributed along the chain; f, g and h are integers; the f/g+h ratio varies from 1 to 10 and the g/h ratio varies from 1 to 10;

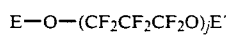

wherein E and E', like or different from each other, represent $CF_3$, $C_2F_5$, $C_3F_7$, $CF_2COF$, $CF_3CF_2COF$ and j represents an integer;

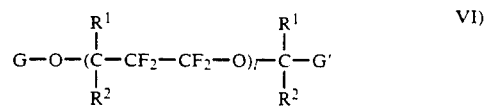

wherein G and G' can be:

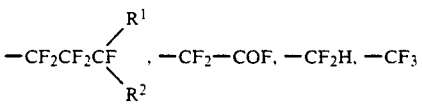

and, furthermore, derivatives of the fluoroacyl function, such as carboxyl and salts thereof, amide, ester, etc.; $R^1$ and $R^2$, like or different from each other, are selected from H, Cl, and an alkyl radical containing from 1 to 3 carbon atoms. When the compound contains different units:

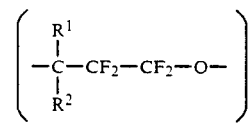

these units are statistically distributed along the chain;

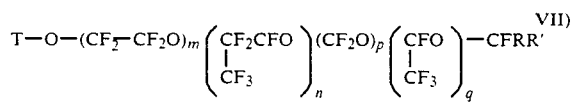

wherein: T is a perfluoroalkyl group containing a Ci atom, in particular it can be:

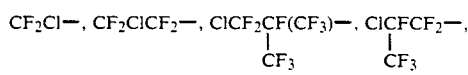

R and R', like or different from each other, are fluorine or chlorine; indexes m, n, p, q are integers and can also be zero, provided that, when m ranges from 1 to 20, n/m is equal to 0.2-2 and when n=0 also q=0. The last class is described in European patent application 0089107957.

According to an effective embodiment of the invention, a perfluoropolyether portion or a fluoropolyether portion is fed to a reactor connected with a distiller, the reactor being then heated to the desired temperature in the presence of the catalytic system which is the object of the present invention. After a short induction time, which can vary depending on the temperature, the substrate to be cleaved, the type of catalyst system utilized, but which time, indicatively, at a temperature of 280° C., generally ranges from 1 to 30 minutes approximately, the substrate cleavage begins, which is apparent from the formation of distillable liquids and gaseous by-products. Now, a gradual continuous feeding of the oil substrate begins, the level in the reactor being kept constant. At the same time, the cleavage products are distilled and the fraction corresponding to the non-cleaved and/or insufficiently cleaved starting oil is recycled.

A characteristic of the catalysts according to the present invention resides in that the oil amount which can be processed before observing a decrease of the catalytic activity is much higher than that obtained with the conventional catalysts: up to 5 kg per gram of catalyst as compared to 0.4 kg per gram of catalyst with $AlF_3$ prepared by fluorination of alumina prevailingly containing the gamma and delta forms.

Another characteristic is the specific productivity, which can reach levels of the order of 0.1 kg/g of catalyst/hour at 300° C., as compared to 0.02 kg/g of catalyst/hour obtained with $AlF_3$.

The exhausted catalysts, recovered on conclusion of the reactions, contain more or less considerable amounts of carbonaceous substances and the inorganic portion still contains silicon dioxide in lower amounts as compared with the starting silicon dioxide, the metal fluoride or oxyfluoride which had been fed. The material has a complex structure. A portion of the fluorides can be recognized as a crystalline species, which is identifiable by means of the usual analysis techniques, while another portion remains in an amorphous form.

EXAMPLES

The present invention will be now illustrated with more details by reference to the following examples, which are given, however, merely for illustrative purposes.

Examples 2 and 4 were carried out, for comparative purposes, using an $AlF_3$ catalyst according to the known technique, and prove respectively the lower yields, the lower productivity and the shorter life of the catalyst which were obtained in such manner with respect to the ones resulting from the other examples according to the present invention.

In the examples, PFPE = perfluoropolyether.

EXAMPLE 1

Into a glass reactor of 0.1 liter volume and equipped with a glass distillation column of 20 cm ($\phi = 2.5$ cm) packed with 5 mm Raschig rings, there were charged 80 g of PFPE of type I, wherein A, A' = $CF_3$, $C_2F_5$, b = 0 and a/c = 10.9, having a viscosity of 251 cSt and an average molecular weight of about 3.600. To the PFPE charge, 7.5 g of $SiO_2/Al_2O_3$ (Akzo Chemie, having a content of 25% by weight of $Al_2O_3$ and a specific surface area of 525 $m^2/g$) were added. The whole was then brought to a reaction mass temperature of 278° C., and the above indicated PFPE began to be continuously fed at a flowrate of 318 g/h. The mixture of volatile products which was generated from the reaction mass passed through the column and the heavier products were recycled to the boiler. The head temperature at the top of the column was maintained around 120°-140° C. A distillate having an average molecular weight of 689, in an amount equal to 65.3% of the fed product, was so obtained. Distillation by-products consisted of uncondensable gases essentially consisting of CO, $CF_4$ and $C_2F_6$. The operation was conducted continuously during 176 minutes without altering the operative conditions.

On conclusion of the operation, the catalyst was recovered by filtration and washing. The catalyst was subjected to analysis, which revealed that the $SiO_2$ content was corresponding to 30% of the starting content (X-ray fluorescence analysis): the sample analysis revealed furthermore a fluorine content equal to 45% by weight and its surface area was equal to 75 $m^2/g$.

EXAMPLE 2 (COMPARISON TEST)

In the same apparatus described in example 1, 15 g of the $AlF_3$ described in patent EP-167,258 were added to the PFPE charge as per example 1. The whole was brought to a reaction temperature of 258° C. and a continuous feeding of PFPE at a flowrate of 387 g/h was started. The head temperature of the column was maintained around 120°-140° C. A distillate was obtained in an amount equal to 57.7% of the fed product; the distillate had an average molecular weight equal to 699. The test was conducted continuously for 147 minutes.

A comparison between example 1 and example 2 proves that, by operating under suitable conditions for obtaining products having the same characteristics, higher yields are obtained with catalysts based on mixed oxides with respect to $AlF_3$.

EXAMPLE 3

The test was conducted using the same apparatus and operative modalities analogous with those of example 1. To a basis of about 80 g of PFPE there were added 2.3 g of $SiO_2/Al_2O_3$ of the same type as the one in example 1.

After having reached a temperature of 271° C., the PFPE already described in example 1 was continuously fed. By keeping the head temperature of the column around 90°-110° C., the feed flowrate was in this case of 281 g/h. The distillate so obtained had an average molecular weight of 608 and the yield was equal to 64.8% based on the fed product. The test was conducted continuously for 30.4 hours. During this stretch of time the catalyst activity was nearly constant.

EXAMPLE 4 (COMPARISON TEST)

Under the same operative conditions as shown in Example 3, there were utilized 2.3 g of an $AlF_3$ of the same type as that utilized in example 2. When a temperature of 272° C. was reached, same PFPE was fed continuously. By keeping a temperature of 100°-110° C. at the column head, the feed flowrate was of 123 g/h. A distillate having an average molecular weight equal to 578 was obtained. In this case, the distillate yield was equal to 53.2% referred to the fed product. The test was conducted continuously for 8.8 hours, whereafter the catalyst activity rapidly decreased. A comparison between example 3 and example 4 proves that, in the obtainment of distillates very similar to each other, in the case of the mixed $SiO_2/Al_2O_3$ oxide, higher yields, a higher productivity and a longer catalyst life were obtained with respect to $AlF_3$.

EXAMPLE 5

Into the same apparatus used in example 1 there were charged 80 g of a PFPE of type IV, wherein A, A' = $CF_3$, COF, f/g/h = 5.01/3.34/1.00, having a viscosity of 86 cSt and an average molecular weight equal to 2300, and 7.5 g of $SiO_2/Al_2O_3$ of the same type as the one utilized in example 1. The whole was brought to a reaction temperature of 250° C., then the same PFPE described before was continuously fed at a flowrate of 172 g/h. The temperature at the column head was maintained around 90°-100° C. A distillate having an average molecular weight of 540 was so obtained. The distillate yield was equal to 76.3% based on the fed product. The test was continuously conducted for 324 minutes.

EXAMPLE 6

According to the modalities already described in example 1, there were charged 80 g of PFPE of type V, wherein E, E' = C$_2$F$_5$, C$_3$F$_7$, having a viscosity of 58 cSt and an average molecular weight equal to 2,700, 10 g of SiO$_2$/Al$_2$O$_3$ of the same type as the one utilized in example 1. The whole was brought to a reaction temperature of 300° C. and the abovesaid PFPE was continuously fed at a flowrate of 128 g/h. The temperature at the column head was maintained at 120°-140° C. and the distillate was obtained in an amount equal to 88.2% referred to the fed product. Its average molecular weight was equal to 540. The test was conducted for a total 475 minutes.

EXAMPLE 7

According to the modalities already described in example 1, 80 g of PFPE of type II having a viscosity of 567 cSt and an average molecular weight of 13,000 were charged. In said PFPE, B, B' = CF$_3$, COF, d/e = 0.63. 2.3 g of SiO$_2$/Al$_2$O$_3$ of the same type as the one utilized in example 1 were then charged. The whole was heated to a reaction temperature of 230° C. and the abovesaid PFPE was continuously fed at a flowrate of 324 g/h. The temperature at the column head was kept around 40°-50° C. A distillate was then obtained with a yield equal to 32% referred to the fed product. The average molecular weight of the distillate was equal to 380. The test was continuously conducted for total 171 minutes.

EXAMPLE 8

Following the modalities of example 1, 80 g of PFPE of the type described in example 1 and 2.3 g of catalyst were charged. As a catalyst, there was used an acid zeolite of type Y in the form of a fine powder with a specific surface area of 900 m$^2$/g, prepared by calcination of LZ Y 62 LINDE in ammoniacal form, marketed by UNION CARBIDE (SiO$_2$/Al$_2$O$_3$ = 5 moles/mole). The whole was brought to a temperature of 274° C. and the abovesaid PFPE was continuously fed at a flowrate of 119 g/h. The temperature at the column head was maintained around 110°-130° C. Finally, a distillate was obtained with a yield equal to 62.5% referred to the fed product. The distillate had a molecular weight equal to 594.

The test was conducted continuously for total 380 minutes.

EXAMPLE 9

Following the modalities already described in example 1, 80 g of PFPE of type II having a viscosity equal to 96.3 cSt and an average molecular weight of 7,000 were charged. In said PFPE, B, B' = CF$_3$, COF, d/e = 1.03. Subsequently, 2.3 g of Cr$_2$O$_3$ carried on SiO$_2$ (20% of Cr$_2$O$_3$) were charged. It was heated up to a reaction temperature of 254° C. and the abovesaid PFPE was continuously fed at a flowrate of 112 g/h. The temperature at the column head was maintained around 98°-105° C. A distillate was then obtained with a yield equal to 75.2% referred to the fed product; its average molecular weight was equal to 584. The test was conducted continuously for total 215 minutes.

EXAMPLE 10

Operating according to the modalities already described in example 1, there were charged 80 g of PFPE of type II having a viscosity of 200 cSt and an average molecular weight equal to 9,000. In said PFPE, A, A' = CF$_3$, CF$_3$CF$_2$, d/e = 0.82. 5 g of V$_2$O$_5$ carried on SiO$_2$ (10% of V$_2$O$_5$) were then charged. The whole was heated up to a reaction temperature of 281° C. and the abovesaid PFPE was continuously fed. The temperature at the column head was maintained around 140° C. A distillate was then obtained with a yield equal to 81.2% referred to the fed product. It exhibited an average molecular weight equal to 680. The test was carried out continuously for total 131 minutes and the feed flowrate was of 241 g/h.

EXAMPLE 11

A catalyst consisting of AlF$_3$ on silica gel was prepared by dissolving hydrated alumina in aqueous HF at 15% up to saturation and by impregnating with this freshly prepared solution an equal weight amount of commercial microporous silica (Akzo F7) having a specific surface area of 285 m$^2$/g. The product was dried at 300° C., so obtaining a catalyst which contained 38% of AlF$_3$.

172 g of a perfluoropolyether of type I, in which A, A' = CF$_3$, C$_2$F$_5$, b = 0 and a/c = 22, having a viscosity equal to 53.5 cSt and an average molecular weight equal to 1,800, were charged into a 250 ml flask along with 2.0 g of the catalyst as specified hereinabove; the flask was equipped with a magnetic stirrer, a distillation head and a cooler.

The mixture was gradually heated and at a temperature of 275° C. the reaction product began to distill. The test was concluded when all the starting product had reacted and the temperature had reached 290° C.

Finally, a distillate was recovered with a yield equal to 89% by weight based on the charged oil; the distillate had an average molecular weight equal to 783. The catalyst, after recovering and washing, exhibited a specific surface area of 235 m$^2$/g.

EXAMPLE 12 (COMPARISON TEST)

174 g of the same perfluoropolyether of the preceding example were charged into a 250 ml flask along with 2.0 g of AlF$_3$ as per example 2. The flask was equipped with a magnetic stirrer, a distillation head and a cooler.

The mixture was gradually heated and, once a temperature of 280° C. was reached, the reaction product began to distill. The test was concluded when all the starting product had reacted and the temperature in the boiler had reached 310° C. On conclusion of the reaction, a distillate having an average molecular weight equal to 966 was recovered in an amount equal to 79% referred to the charged oil.

EXAMPLE 13

Example 3 was repeated. After a 10 hour reaction, 1820 g of product were obtained, which was treated with excess CaO to neutralize present acids. The reaction mixture was then steam distilled under atmospheric pressure. The distillate was separated from water by obtaining 974 g of product free from functional groups.

The neutral product was further rectified under atmospheric pressure and the fraction having b.p. 66°-67° C. collected (234 g).

Gas-chromatography showed a 93% purity. NMR analysis showed this fraction a perfluoro-2,5-dimethyl-1,4-dioxane and perfluoro-2,6-dimethyl-1,4-dioxane mixture. Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference .

We claim:

1. A process for reducing the molecular weight of fluoropolyethers or perfluoropolyethers having neutral and/or functional end groups by selective catalytic cleavage, comprising conducting said cleavage at a temperature ranging from 150° C. to 380° C., in the presence of a catalyst system consisting of a combination of silicon dioxide with at least an oxide, a fluoride or an oxyfluoride of a metal selected from Al, Ti, V, Cr, Co, Fe, Ni, Mo, Zn, Cu, Cd, Mn, Sb, Sn, Zr, Sc, Y, Pb, Mg, W, La and homologs thereof.

2. The process according to claim 1, wherein said combination is a mixed oxide in the form of a silicate of a metal selected among those defined in claim 1, in a microcrystalline or amorphous form.

3. The process according to claim 1, wherein said combination is a mixed oxide consisting of chemically homogeneous amorphous mixtures of $SiO_2$ and of the metal oxide.

4. The process according to claim 1, wherein said combination is a mixed oxide consisting of at least one metal oxide carried on silicon dioxide.

5. The process according to claim 1, wherein said combination consists of at least a fluoride selected from those defined in claim 1, carried on $SiO_2$.

6. The process according to claim 1, wherein said combination consists of at least an oxyfluoride selected from those defined in claim 1, carried on $SiO_2$.

7. The process according to claim 1, wherein said combination is selected from silicon dioxide-alumina, silicon dioxide-titanium oxide, a combination of silicon dioxide and aluminum oxide in the form of aluminum silicates having zeolitic structure in acid form, silicon dioxide-chromium oxide, chromium oxide on silicon dioxide in the form of silica gel, silicon dioxide-$V_2O_5$, $AlF_3$ on silicon dioxide, LaOF and $ZrOF_2$ on silicon dioxide.

8. The process according to claim 1, wherein the silicon dioxide content, expressed as $SiO_2$, ranges from 10% to 95% by weight of the catalytic combination.

9. The process according to claim 8, wherein the silica content, expressed as $SiO_2$, ranges from 50% to 90% by weight of the catalytic combination.

10. The process according to claim 1, wherein the specific surface area of the catalytic combination is greater than 10 $m^2/g$.

11. The process according to claim 1, wherein said catalytic combination is introduced in the form of a fine powder having an average particle size below 0.1 mm.

12. The process according to claim 1, wherein said catalytic combination is utilized in an amount ranging from 0.1% to 25% by weight based on the weight of the starting perfluoropolyether or fluoropolyether.

13. The process according to claim 12, wherein said catalytic combination is utilized in an amount ranging from 0.5% to 10% by weight based on the weight of the starting perfluoropolyether or fluoropolyether.

14. Process for the preparation of perfluoro-2,5-dimethyl-1,4-dioxane and perfluoro-2,6-dimethyl-1,4-dioxane comprising selectively cleaving a perfluoropolyether having the formula:

$$A-O(CF_2-CFO)_a(CF-O)_b(CF_2O)_c-A'$$
$$\quad\quad\quad\quad\quad\; |\quad\quad\quad\; |$$
$$\quad\quad\quad\quad\; CF_3\quad\; CF_3$$

wherein A and A', like or different from each other, represent a perfluoroalkyl group containing from 1 to 3 carbon atoms, $CF_3$,

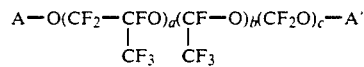

units 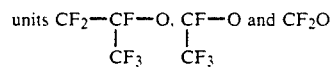

are statistically distributed along the chain; a and c are integers, while b is an integer or zero and the a/b+c ratio varies from 5 to 15, by cleaving at a temperature between 150° C. and 380° C. in the presence of a silicon dioxide catalyst system consisting of a combination of silicon dioxide with at least an oxide, a fluoride or an oxyfluoride of a metal selected from Al, Ti, V, Cr, Co, Fe, Ni, Mo, Zn, Cu, Cd, Mn, Sb, Sn, Zr, Sc, Y, Pb, Mg, W, La and homologs thereof, distilling the resulting products and collecting a b.p. 66°–67° C. fraction from the distilling step.

* * * * *